United States Patent [19]

Widmer et al.

[11] Patent Number: 5,411,942
[45] Date of Patent: May 2, 1995

[54] PEPTIDE DERIVATIVE, PHARMACEUTICAL PREPARATION CONTAINING IT AND METHOD FOR TREATMENT OF GLAUCOMA

[75] Inventors: Fred Widmer, Dee Why, Australia; Kailash K. Gauri, Lentfohrden; Stig Aasmul-Olsen, Skodsborg, both of Denmark

[73] Assignee: Carlbiotech Ltd. A/S, Copenhagen, Denmark

[21] Appl. No.: 859,714

[22] PCT Filed: Dec. 7, 1990

[86] PCT No.: PCT/DK90/00322

§ 371 Date: Jul. 20, 1992

§ 102(e) Date: Jul. 20, 1992

[87] PCT Pub. No.: WO91/09053

PCT Pub. Date: Jun. 27, 1991

[30] Foreign Application Priority Data

Dec. 7, 1989 [DK] Denmark ............................ 6158/89

[51] Int. Cl.6 ...................... A61K 37/00; A61K 37/02; C07K 5/00; C07K 7/00
[52] U.S. Cl. ............................................ 514/17; 514/8; 514/9; 514/11; 530/330; 530/317; 530/322
[58] Field of Search ................ 530/330, 331, 317, 322; 514/8, 9, 11, 17, 18

[56] References Cited

U.S. PATENT DOCUMENTS

| | | | |
|---|---|---|---|
| 4,457,489 | 10/1985 | Goldstein et al. | 514/11 |
| 4,559,340 | 12/1985 | Neustadt et al. | 514/22 |
| 4,634,698 | 1/1987 | Andrews et al. | 514/22 |

FOREIGN PATENT DOCUMENTS

| | | |
|---|---|---|
| 0088350A1 | 9/1983 | European Pat. Off. . |
| 0291999A2 | 11/1988 | European Pat. Off. . |
| 0311012A2 | 4/1989 | European Pat. Off. . |
| 0320204A2 | 6/1989 | European Pat. Off. . |
| 8604217A2 | 7/1986 | WIPO . |

OTHER PUBLICATIONS

Bodanszky, *Int J. Peptide Protein Res.* vol. 25, pp. 449–474, (1985).
Komoriya et al., *Proc. Natl. Acad. Sci.* vol. 81, pp. 1351–1355, Mar. 1984.
Kunzek et al., *Chem. Abstrs.*, vol. 93, No. 3, p. 745, #26819u, (1979).
Kaufman et al., *Chem Abstrs*, vol. 93, No. 1, p. 790, #8522n, (1980).
Camble et al., *Chem. Abstrs.*, vol. 88, No. 5, p. 535, #38139g, (1978).
Coakes and Holmer Sellars, 1985, "An Outline of Opthalmology" (Wright, Bristol, UK) pp. 54–57.
Kaufman, 1984, in *Current Topics in Eye Research*, (eds. Zadunaisky and Davson) vol. 4: 97–138.
Sugrue and Smith, 1985, in *Ann. Rpts. in Medicinal Chemistry*, (Acad. Press) vol. 20: 83–91.
Weiner, 1980, in *The Pharmacological Basis of Therapeutics*—6th edition, pp. 138–155.
Taylor, 1990, in *The Pharmacological Basis of Therapeutics*—8th edition, pp. 113–116, 143–146.
Smith, C. S. et al., 1988, Drug Development Res. 15: 371–379.
Sisto, et al., 1980, in *Peptides, Chemistry, Structure and Bio.*, (Escom, Leiden, eds), pp. 722–773.
Widmer and Johansen, 1979, Carlsberg Res. Commun, 44: 37–46.
Widmer and Johansen, 1985, in *Synth. Peptides in Bio. and Med.*, (Elsevier, Amsterdam) pp. 79–86.
Alakhov et al., 1988, in *Peptides 1988, Proc. 20th Eur. Pep. Symp.*, pp. 286–337.
Diestelhorst and Krieglstein, 1989, Fortschritte der Ophthalmologie, 89: 89–91.

*Primary Examiner*—Jill A. Warden
*Assistant Examiner*—A. M. Davenport
*Attorney, Agent, or Firm*—Allegretti & Witcoff, Ltd.

[57] ABSTRACT

Peptide derivatives of 3–5 optionally substituted amino acids, a process for preparing the peptides, a pharmaceutical composition containing at least one peptide derivative active against glaucoma and intraocular hypertension and a method for treating glaucoma and intraocular hypertension.

3 Claims, No Drawings

PEPTIDE DERIVATIVE, PHARMACEUTICAL PREPARATION CONTAINING IT AND METHOD FOR TREATMENT OF GLAUCOMA

The present invention relates to hitherto unknown peptide derivatives, a process for the preparation thereof, pharmaceutical preparations containing these derivatives and a method for the treatment of glaucoma.

Glaucoma is a very common eye disease affecting millions of people in the later stages of their life. Glaucoma is characterized by abnormally high intraocular pressure and, if untreated, damage of the optic nerves which may cause narrowing of the visual field, and eventually irreversible blindness.

The intraocular pressure is determined by the rates of inflow and outflow, i.e. the dynamics of the aqueous humor. The aqueous humor enters into the posterior chamber of the eye, and then flows through the pupil to the anterior chamber, from where it eventually leaves the eye through the trabecular meshwork.

The aqueous humor supplies nutrients to the lens and cornea, and its proper supply is thus of the utmost importance to maintain healthy eye.

Any disturbance of aqueous humor dynamics by either excess inflow, or reduced outflow, results in a rise of the intraocular pressure above the normal value (for adults) of 17–20 mm Hg, i.e. the eye becomes hypertensive. A prolonged hypertensive state will result in nerve damage and blindness. Detailed descriptions on glaucoma can be found in "An Outline of Ophthalmology", by R. L. Coakes, and P. J. Holmer Sellars, published by Wright Bristol (1985), cf. pp. 54/57, and in the series: Current Topics in Eye Research", edited by J. A. Zadunaisky and K. Davson, Academic Press.

All known antiglaucoma drugs on the market lower the intraocular pressure, either by decreasing formation of aqueous humor, or by increasing the outflow, i.e. the elimination of aqueous humor from the eye. Glaucoma drugs are thus all hypotensive agents.

The most common class of antiglaucoma agents are adrenergic antagonists; many of them are β-blockers (the most widely used of this type is timolol), adrenergic, agonists, dopaminergic agents, cholinergic agents (the most widely used of this type is pilocarpine), and several other classes of compounds. For detailed overviews, see for example Annual Reports in Medicinal Chemistry, Vol. 20, chapter 9: "Antiglaucoma Agents", by M. F. Sugrue and R. L. Smith (1985, Academic Press), and the text: "The Pharmacological Basis of Therapeutics" by A. Goodman and L. Gilmans.

One of the characteristics of glaucoma drugs is thus the fact that an enormously wide variety of chemical structural types can be used to reduce excessively high intraocular pressure.

None of the currently used drugs is fully satisfactory. There are serious side effects affecting the heart, the kidneys, the lungs and the libido. Furthermore, there are problems of metabolic stability which necessitates several applications of eye drops per day. Great efforts are therefore made to develop new antiglaucema agents which would be free of the above constraints. Recently, an entirely new chemical structural type of compounds, namely peptides and peptide derivatives, was described as having antiglaucoma acitivity, i.e. as hypotensive agents. Examples are carboxyal aldipeptides (European Patent No. 0088350) and the atrial natriuretic factor, a long peptide of 29 amino acids in length (Fortschritte der Ophthalmologie, Volume 89, pp. 89/91 (1989)).

Furthermore, hydrolysates of milkproteins were also described as having antiglaucoma activity (WO 86/04217).

The present invention describes hitherto unknown synthetic peptides consisting of up to 5 amino acids, and derivatives thereof, which lowers the intraocular pressure in a relevant animal model.

The present invention thus concerns a peptide derivative having the general formula

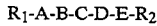

$$R_1\text{-}A\text{-}B\text{-}C\text{-}D\text{-}E\text{-}R_2 \qquad \text{I}$$

or a N—C cyclic form thereof, or a disulfide bridged, N—C cyclic or linear dimer thereof, wherein A is absent or is a non-hydrophobic, uncharged D- or L-amino acid or a desamino-derivative thereof, which optionally is mono- or disubstituted on the nitrogen of the amide side chain with straight, branched, cyclic, substituted or unsubstituted alkyl, aralkyl or aryl, all of which are optionally mono- or polysubstituted with halogen, nitro, amino, sulfo, phospho or carboxyl, and each aralkyl- and arylsubstituent may further be alkyl substituted, B is absent or is an uncharged amino acid or an uncharged N-methylated amino acid, C is an uncharged amino acid or an uncharged N-methylated amino acid, D is an uncharged amino acid with a non-hydrophilic or absent sidechain, E is cysteine or a cysteine homologue, the sulfhydryl group being free or substituted by either —$CR_3R_4NHCOCR_5$, where $R_3$ and $R_4$ are independently H or halogen, and $R_5$ is straight, branched or cyclic alkyl, aralkyl or aryl, all of which are optionally mono- or polysubstituted with halogen, carboxyl, sulfo, phospho, amino or nitro, and each aralkyl- and arylsubstituent may further be alkyl substituted, —$S$—$CR_6R_7R_8$, wherein $R_6$, $R_7$ and $R_8$ are independently H, halogen, straight, branched or cyclic alkyl, aralkyl or aryl, all of which are optionally mono- or polysubstituted as indicated for $R_5$, —$CR_9R_{10}R_{11}$, wherein $R_9$, $R_{10}$ and $R_{11}$ are independently H, alkyl, aralkyl or aryl, all of which are optionally mono- or polysubstituted as indicated for $R_5$, or E is an optionally substituted decarboxy derivative of cysteine or homologues thereof, $R_1$ is H or R—CO, where R is H, straight, branched or cyclic alkyl up to C20, optionally containing double bonds and/or substituted with halogen, nitro, amino, sulfo, phospho or carboxyl, or aralkyl or aryl optionally substituted as listed for the alkyl and further including alkyl, or glycosyl, nucleosyl or $R_1$ is an L- or D-α amino acid or $R_1$ is absent when A is an unsubstituted desamino-derivative, or when the peptide is a N—C cyclic form, and $R_2$ is —$NR_{12}R_{13}$, wherein $R_{12}$ and $R_{13}$ are independently H, straight, branched or cyclic alkyl, aralkyl or aryl optionally substituted as defined for $R_5$, —OR$_{14}$, where R$_{14}$ is H, straight, branched or cyclic alkyl, aralkyl or aryl, optionally substituted as defined for R$_5$, —O—glycosyl, or an L- or D-α-amino acid or R$_2$ is absent, when E is a decarboxy derivative of cysteine or a homologue thereof or the peptide is a N—C cyclic form or a peptide of the corresponding formula containing one or more retroinverse, ketomethylene or methylsulfide peptide bends.

In a preferred group of derivatives according to the invention

A is selected from the group consisting of Asn, Ser, Gln, Gly, Pro, Sar, Thr, Ala and the corresponding N-alkylated amino acids, B is selected from the group consisting of Gly, Ala, Leu, Pro, Sar, Ser, Met, Thr and the corresponding N-alkylated amino acids, C is selected from the group consisting of Ser, Gly, Pro, Sar, Leu, Met, Thr and the corresponding N-alkylated amino acids, D is selected from the group consisting of Val, Gly, Thr, Ala, His, Ile, Leu, N-Leu, N-Val, Met, tert.-Leu and aromatic amino acids, and E, R$_1$ and R$_2$ have the meaning stated in claim 1.

Especially preferred derivatives according to the invention are peptide derivatives wherein A is Asn,
B is Gly,
C is Gly,
D is Val,
E is Cys(Acm),
R$_1$ is H, and
R$_2$ is NH$_2$ wherein A is Asn,
B is Leu,
C is Gly,
D is Val,
E is Cys(Acm),
R$_1$ is H, and
R$_2$ is NH$_2$, wherein A is Asn,
B is Ala
C is Gly
D is Val,
E is Cys(Acm),
R$_1$ is H, and
R$_2$ is NH$_2$, wherein A is absent,
B is Asn,
C is Leu,
D is Gly,
E is Cys(Acm),
R$_1$ is H, and
R$_2$ is NH$_2$,
wherein A is absent,
B is absent,
C is Gly,
D is Val,
E is Cys(Acm),
R$_1$ is acetyl, and
R$_2$ is NH$_2$, and wherein A is absent,
B is absent,
C is Asn,
D is Val,
E is Cys(Acm),
R$_1$ is H, and
R$_2$ is NH$_2$.

The invention also concerns a process for preparing the compounds according to any of the preceding claims, characterized in that one synthesizes in a manner known per se in the peptide chemistry from the corresponding protected amino acids the protected peptides, and in a manner known per se optionally one splits off from these the protective group(s).

A preferred process is characterized in that one acylates the C-terminal amino acid or a peptide fragment of the peptide to be prepared, containing the C-terminal amino acid, optionally protected in the side function, or a derivative of this C-terminal amino acid or of this peptide fragment protected in another way on the carboxylic group with a derivative protected on its terminal nitrogen atom and optionally in the side function and activated on the carboxyl group of the amino acid preceeding in the amino acid sequence of the peptide to be prepared or with a peptide fragment derivative containing the amino acids preceeding in the amino acid sequence of the peptide to be prepared, and protected on its terminal nitrogen atom and optionally in the side function and activated on the carboxyl group and optionally in (one) next step(s) one carries out a further or further acylation(s) with the obtained peptide intermediate protected on the terminal nitrogen atom and the further peptide intermediate(s) protected on the terminal nitrogen atom obtained by (a) possible further such acylation(s) after elimination in a manner known per se of the protective group of the terminal nitrogen atom to be acylated with the or each of the derivative(s) protected on its terminal nitrogen atom and activated on its carboxyl group of the amino acid preceeding in the amino acid sequence of the peptide to be prepared or with a peptide fragment protected on its terminal nitrogen atom and optionally in the side function and activated on the carboxyl group and containing the amino acids preceeding in the amino acid sequence of the peptide or salt, complex, amide or alkyl ester, respectively, of it to be prepared carrying out so much acylations as it is necessary to attain the desired amino acid sequence and optionally one eliminates in a manner known per se from the obtained protected peptide the protective group of the terminal nitrogen atom and the possible other protective group(s).

Further the invention concerns a pharmaceutical composition containing a peptide derivative according to the invention in an amount effective to treat glaucoma and a pharmaceutically acceptable diluent or excipient.

Additionally the invention concerns a method for treating glaucoma and intraocular hypertension, comprising administering to a mammal an effective anti-glaucoma or eye pressure lowering amount of a peptide derivative according to the invention.

The peptide derivatives of this invention are preferably used in topically applicable aqueous isotonic and sterile solutions or in sterile solutions or dispersions in an oil as used for the topical treatment of the eye. A typical oil for ocular treatment is sterile castor oil. These topical solutions or dispersions contain 0,1–10%, in particular 0,2–5%, preferably 0,25–1% (percent by weight) of at least one of the peptide derivatives of this invention. The normal dosage of these solutions is 1 to 5 drops administered to the conjunctival sac of the eye. This dosage is normally administered 2 to 6 times per day. [20 drops of a DAB-9 dropper (Tropfenzähler gemäss "Deutsches Arzneibuch 9") will give about 1 ml].

An especially effective peptide for treating glaucoma has the formula

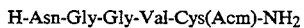
H-Asn-Gly-Gly-Val-Cys(Acm)-NH₂ where
H = free N-terminal amino group
Asn = Asparagine
Gly = Glycine
Val = Valine
Cys = Cysteine
Acm = Acetamidomethyl-
—NH₂ = C-terminal carboxylamide This novel peptide and its structurally related active derivatives are described in claim 1. The term amino acid is to be understood to not only cover the 20 natural amino acids, but also to embrace amino acid replacements and substituents as recognized in the art.

The term peptide is to be understood to embrace peptide bond replacements and/or peptide mimetics, i.e. pseudopeptides, as recognized in the art (see for example: Proceedings of the 20th European Peptide Symposium, edt. G. Jung, E. Bayer, pp. 289–336, and references therein), as well as salts and pharmaceutical preparations and/or formulations which render the bioactive peptide(s) particularly suitable for topical application as drops, or for oral delivery. Such salts, formulations, amino acid replacements and pseudopeptide structures may be necessary and desirable to enhance the stability, formulation, deliverability, or to improve the economy of production, and they are acceptable, provided they do not negatively affect the required biological activity of the peptide as a hypotensive agent suitable for the treatment of elevated intraocular pressure and glaucoma.

Apart from substitutions, three particular forms of peptide mimetic and/or analogue structures of particular relevance when designing bioactive peptides, which have to bind to a receptor while risking the degradation by proteinases and peptidases in the blood and elsewhere, may be mentioned specifically, illustrated by the following examples: Firstly, the inversion of backbone chiral centres leading to D-amino acid residue structures may, particularly at the N-terminus, lead to enhanced stability for proteolytical degradation while not impairing activity. An example is given in the paper "Tritriated D-ala¹-Peptide T Binding", Smith, C. S. et al, Drug Development Res. 15, pp. 371–379 (1988). Secondly, stability and sometimes also receptor binding may be enhanced by forming cyclic analogues. An example of this is given in "Conformationally restricted thymopentin-like compounds", U.S. Pat. No. 4,547,489 (1985), Goldstein, G. et al. Finally, the introduction of ketomethylene, methylsulfide or retroinverse bonds to replace peptide bonds, i.e. the interchange of the CO and NH moieties may both greatly enhance stability and potency. An example of the latter type is given in the paper "Biologically active retroinverso analogues of thymopentin", Sisto A. et al in Rivier, J. E. and Marshall, G. R. (eds.) "Peptides, Chemistry, Structure and Biology", Escom, Leiden (1990), p. 722–773.

The peptides of the invention can be synthesized by various methods which are known in principle, namely by chemical coupling methods (cf. Wunsch, E.: "Methoden der organischen Chemie", Volume 15, Band 1+2, Synthese von Peptiden, Thieme Verlag, Stuttgart (1974), and Barrany, G.; Merrifield, R. B.: "The Peptides", eds. E. Gross, J. Meienhofer., Volume 2, Chapter 1, pp. 1–284, Academic Press (1980)), or by enzymatic coupling methods (cf. Widmer, F., Johansen, J. T., Carlsberg Res. Commun., Volume 44, pp. 37–46 (1979), and Kullmann, W.: "Enzymatic Peptide Synthesis", CRC Press Inc., Boca Raton, Fla. (1987), and Widmer, F., Johansen, J. T. in "Synthetic Peptides in Biology and Medicine", eds., Alitalo, K., Partanen, P., Vatieri, A., pp. 79–86, Elsevier, Amsterdam (1985)), or by a combination of chemical and enzymatic methods if this is advantageous for the process design and economy.

The peptide derivatives of the invention can be produced by the above listed general synthetic methods, or by an advantageous combination of them.

The described peptides which constitute this invention can be used for the treatment of glaucoma in pharmaceutical preparations, possibly in combination with pharmaceutical carriers and delivery systems and/or other useful and pharmaceutically acceptable additives.

It was shown in an animal experiment where the intraocular pressure in the rabbit eye was experimentally raised above the normal level, that the antiglaucoma pentapeptide and certain derivatives, which are all covered in claim 1, were able, in a concentration range of 0.1, 0.5 and 1.0%, to achieve an equal or better lowering of the intraocular pressure than the β-blocker timolol (in comparable concentration) which is commonly used to treat glaucoma, but which, however, being a β-blocker has serious side effects on the heart, lungs and sexual functions.

It is anticipated that with the peptides according to the invention, many of these and other side effects can be avoided. Indeed, a particular pentapetpide according to the invention, AsnLeuGlyValCys(Acm)NH₂, has been especially thoroughly examined for side effects, especially blood pressure effects, toxicity and mutagenicity as well as local irritant or anaesthetic effects in a variety of animal and microbial models.

Thus in mice and rats, doses as high as 40 mg/kg intravenously is easily tolerated and no effect on blood pressure is found, e.g. at 10 mg/kg in rats, indicative of no β-blocking action at doses several orders of magnitude higher than the local therapeutic doses expected. Also, no toxic or adverse effects were found by subcutaneous administration of similar doses in rats, also under prolonged treatment for a month. In an Ames test on Salmonella strains, the compound was classified as non-mutagenic. Finally, local topical application of 5% solution as eye drops in rabbit's eye showed neither anaesthetic effects nor irritant effects, even after prolonged treatment over a month.

The animal model on which the intraocular pressure lowering effect of the antiglaucoma peptide(s) was first established, is a clinically relevant model which was developed in the laboratory of one of the inventors who has positively shown on this model the pressure lowering effect of many $\beta$-blockers (such as timolol) and adrenergic agonists, and thus has demonstrated the clinical relevance of the model on known and putative glaucoma drugs.

The main feature of this clinical model is a stress induced elevation of the intraocular pressure in the rabbit eye above the initial and normal value. The stress is exerted, i.e. applied, in the form of measuring the pressure (at 12 hour intervals) with the help of a SHI-OTZ-Tonometer, which is loaded with 7.5 grams. The pressure first begins to rise after 5 measurements, i.e. after 2½ days, and reaches a maximum after 10 measurements, i.e. after 5 days.

Known antiglaucoma drugs lower the intraocular pressure when they are applied after the intraocular pressure (IOP) has clearly been established, in spite of the fact that the trauma, i.e. the measuring of the pressure, continued during the treatment.

If the treatment with the glaucoma drugs is started simultaneously with the traumatization, i.e. the exertion of stress by measuring of the pressure at the start of the animal experiment, the active glaucoma drugs antagonize the development of an elevated intraocular pressure above the initial and normal value, while the inactive compounds will not antagonize, and thus result in an elevated pressure. The relevance of this model has been demonstrated in many experiments with clinically used antiglaucoma drugs.

Detailed descriptions are found in: Stainbach, T., Dissertation, Universitäts-Augenklinik Hamburg-Eppendorf, 1986: "Adrenergica und neue Peptide bei Augeninnendruck: Beziehung zum Prostaglandin im Kammerwasser von Kaninchen". The activity of the antiglaucoma pentapeptide, and its active derivatives, which constitutes this invention, has likewise been demonstrated on this model as shown in the examples. These peptidic compounds are thus likely candidates for the treatment of glaucoma.

The peptides described in the above doctoral thesis are not well defined chemical compounds as are the peptide derivatives of this invention, rather they are mixtures which resulted from the hydrolysis of milk proteins. These peptides and their various activities, among which is antiglaucoma, are described in the European Patent No. 210 204 by one of the present inventors.

The findings of intraocular pressure lowering effects in the stress induced rabbit model has been confirmed and further studied by using another elevated eye pressure rabbit model. In this model, the widely applied water load model, elevation of the intraocular pressure is achieved by injecting a large volume of sterile water intraperitoneally into the rabbits. Following onset of eye drop treatment in one eye while the other eye is treated with saline placebo, the intraocular pressure of both eyes is then measured at various intervals and the pressure difference between the eyes is taken as an expression of the pharmaceutical effect. In these experiments, pilocarpine, a well-known pressure lowering cholinergic agent, was used as positive control.

The advantage of the peptide derivative of the invention is their defined chemical nature, which allows for proper registration and, if deemed desirable, for logic and systematic structural modification to produce analogues of even better properties than the ones invented and claimed now.

Furthermore, the presently invented peptide is of low molecular weight ($\leq 600$), and thus topically applicable, unlike the atrial natriuretic factor described in Fortschritte der Ophthalmologie, Volume 86, p. 89-91 (1989), which has a molecular weight of $\sim 3000$, and needs to be administered by injection to achieve an antiglaucoma effect. Indeed, in vitro studies using freshly excised bulbar conjunctiva and anterior sclera, has demonstrated the penetration of several pentapeptides according to this invention through tissue samples mounted in a lucite-block Ussing chamber suspended in areated gluthatione bicarbonate Ringer's solution. Thus, AsnGlyGlyValCys(Acm)NH$_2$ was found to penetrate both tissues and AsnLeuGlyVAlCys(Acm)NH$_2$ was found to penetrate scleral tissue.

Moreover, the atrial natriuretic factor is a cardiovascular hormone and thus not suited to be used to treat glaucoma over prolonged periods of time. Finally, both the peptidic protein hydrolysate mixtures (which are not necessarily strictly peptidic in chemical structural terms) and the atrial natriuretic factor are of size which may give rise to an immune response followed by the production of antibodies. Such a response is unlikely to occur with the low molecular weight antiglaucoma pentapeptide, and its active derivatives, which constitute the body of this invention. Indeed, it has so far not been possible to detect such antibodies by a response in a ELISA-assay on serum samples from rats treated subcutaneously for one month with AsnLeuGlyVal-Cys(Acm)NH$_2$ in large doses.

The mechanism, or mechanisms, by way of which the peptides according to the invention work, is so far not known in detail and may be of hitherto unknown types or related to some known mechanisms. With the apparent lack of $\beta$-blocking effects, other known mechanisms could be effects on the enzyme carbo-anhydrase or effects on aqueous humour outflow. Some indications of mechanisms of the latter type have been found in in vitro studies. Thus, an in vitro study conducted at an early stage demonstrated that AsnGlyGlyValCys-(Acm)NH$_2$ induced a marked and significant decrease of uptake of glycosamines in cultured bovine trabecular meshwork cells. Cell cultures similarly incubated with the peptide showed normal growth and ultrastructure and no effect was found on collagen and fibronectin synthesis. The significant decrease in glycosamine uptake with normal synthesis of glycoproteins like fibronectin is taken to indicate an influence on the formation of glycosamino glycans, an important parameter in the regulation of outflow of aqueous humour from the eye.

The invention is now further explained and documented with examples.

Synthesis of Antiglaucoma Pentapeptide

The abbreviations used in this description for amino acids and protecting groups are in agreement with the IUPAC-IUB standard rules for nomenclature.

In addition, and in particular, the following abbreviations are used:

HOSu: N-hydroxysuccinimide
—OSu: N-hydroxysuccinimide ester

DCC: Dicyclohexylcarbodiimide
CPD-Y: Carboxypeptidase Y
Boc: tert.-butyloxycarbonyl
OBzl: Benzyl Ester
Acm: Acetamidomethyl ($CH_3CONHCH_2$—)
pTos: p-Toluenesulfonate
DMF: Dimethylformamide
DCU: Dicyclohexylurea
HAc: Acetic Acid
HCOOH: Formic Acid

EXAMPLE 1

SYNTHESIS OF HAc, H—AsnGlyGlyValCys(Acm)—$NH_2$

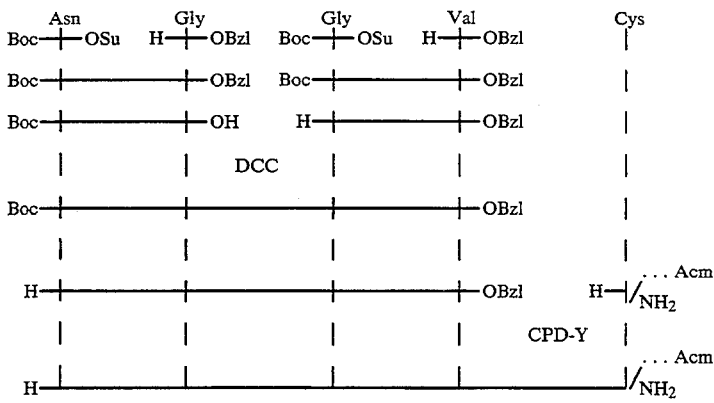

FIG. 1: Overall synthesis scheme

BocAsnGlyOBzl: 58 g BocAsnOH (0.25 moles) and 29 g HOSu are dissolved in 250 ml DMF and cooled to −20°. 52 g DCC dissolved in 250 ml DMF is added. After 4 hours stirring at room temperature 85 g GlyOBzl, pTos and 35 ml TEA is added. After stirring overnight the DCU i filtered off, DMF removed in vacuo on a Rotavap, and the resulting oil dissolved in EtAc. After extraction with sat. NaCl, sat. $NaHCO_3$, and 10% citric acid, the solvent is dried with $Na_2SO_4$ and evaporated. The resulting crystalline ma is dried in a desiccator. Yield: 64 g (67%).

BocGlyValOBzl: 44 g BocGlyOH (0.25 moles) is dissolved in 250 ml DMF, together with 29 g HOSu. After cooling to −20° C. 52 g DCC dissolved in 250 ml DMF is added. After 4 hours stirring at room temperature 95 g ValOBzl, pTos is added together with 35 ml TEA. After stirring overnight at room temperature, DCU is filtered off, DMF removed and the resulting oil taken up in EtAc and washed with sat. NaCl, sat. NaHCO, and 10% citric acid. The EtAc is dried with $Na_2SO_4$, removed by vacuum evaporation and the resulting crystalline mass dried in a desiccator. Yield: 59 g (65%).

BocAsnGlyGlyValOBzl: The 64 g BocAsnGlyOBzl from above is dissolved in 500 ml MeOH and hydrogenated for 20 hours with 5 g 10% Pd-C as catalyst. The catalyst is removed by filtration and the solvent removed to give BocAsnGlyOH. This is dissolved in 200 ml DMF cooled to −20° C. and then activated with 20 g HoSu and 35 g DCC for 2 hours. 59 g Boc-GlyValOBzl is deBoced in HCl-EtAc, the HCl-EtAc removed by evaporation and the resulting oil taken up in 100 ml DMF and neutralized with 24 ml TEA. This is then added to the preactivated BocAsnGlyOSu. The mixture is stirred overnight, DCU removed by filtration and the DMF removed by evaporation. The residue is taken up in EtAc washed with sat. Nacl, sat. $NaHCO_3$, and 10% citric acid. After drying the EtAc with $MgSO_4$, it is removed by evaporation to give a powder, which is dried in a desiccator. Yield: 60 g (70%).

HAc,H-AsnGlyGlyValCys(Acm)/$NH_2$: 12 g BocAsnGlyGlyValOBzl is dissolved in HCl-EtAc-DMF. After 5 hours the solvent is removed by evaporation. The residue is treated with ether and the resulting crystals collected by filtration and dried in a desiccator. Yield 10 g (95%).

The 10 g HCl, H-AsnGlyGlyValOBzl is dissolved in 20 ml DME. This is added batchwise to a solution of 12,1 g Cys(Acm)$NH_2$ in 150 ml 0.1M KCl, 1 mM EDTA, 35 μM CPD-Y, pH 8.0. pH is kept constant during the reaction by addition of 0.5M NaOH. After 5 hours, when HPLC shows that the reaction is finished, the reaction is stopped by taking pH to 3 with HCOOH. The reaction mixture is chromatographed on 2 Prep 500 (Waters) reverse phase columns using 50 mM $CH_3COOH$ as starting buffer and EtOH as organic eluent. Fractions containing product are concentrated by evaporation and finally freeze-dried. Yield: 5.62 g (70%).

| Analysis: | |
| --- | --- |
| Sum. Formula: | $C_{19}H_{35}N_8O_7SCl$ |
| Molecular Weight: | 555.057 |
| Mwt (free base): | 518.56 |
| FAB-MS: | 519: M+ =[H—AsnGlyGlyValCys(Acm)$NH_2$]+ 448: M+.-Acm=H—AsnGlyGlyValCys$NH_2$]+ (Acm = 71) |

Amino Acid Analysis a) 6N HCl: Asp(0.9), Gly(2.0), Val(1.0), Cys destroyed b) Amino peptidase M: Asn(0.9), Gly(2.0), Val(1.1), Cys(Acm) (1.1)

HPLC analysis on a system with 2 Waters 600A pumps, Waters 480 Detector, Waters 660 solvent programme, Waters UK 6 injector and a Hewlett-Packard 3390A recorder/integrator and under the following conditions showed that the sample is at least 95% pure:

Sample: 30 μl, conc. ca. 4 mg/ml
Column: 8C18 10 μm
A-Buffer: TEAP pH 3

B-Buffer: 80% CH$_3$CN, 20% TEAP
Elution program: 2% B to 50% B in 20 minutes using a linear gradient
Temperature: 20°-25° C.
Pressure: ca. 1000 psi
Flow rate: 2 ml/min.
Chart speed: 0.5 cm/min.
Wave-length: 230 nm
AUFS: 0.2
Attenuation: 3

EXAMPLE 2

H-Asn-Leu-Gly-Val-Cys(Acm)-NH$_2$ was prepared in an analogous way and analysed in the same way as in example 1.

HPLC analysis showed that the product was more than 95% pure.

Amino Acid analysis: Asp (1.00)*), Leu (0.95), Gly (0.95), Val (0.85), Cys (0.65)**)

*) Asn is hydrolysed to Asp during the acid hydrolysis of the sample
**) Cys is partially destroyed during the acid hydrolysis of the sample

EXAMPLE 3

HAc, H-Asn-Ala-Gly-Val-Cys(Acm)-NH$_2$ was prepared in an analogous way and analysed in the same way as in example 1.

HPLC analysis showed that the product was mores than 95% pure.

Amino Acid analysis: Asp (1.10)*), Ala (1.00), Gly (0.95), Val (0.90), Cys (0.70)**)

*) Asn is hydrolysed to Asp during the acid hyudrolysis of the sample
**) Cys is partially destroyed during the acid hydrolysis of the sample

EXAMPLE 4

Synthesis of HAc, H—Asn—Leu—Gly—Val—Cys(Acm)—NH$_2$

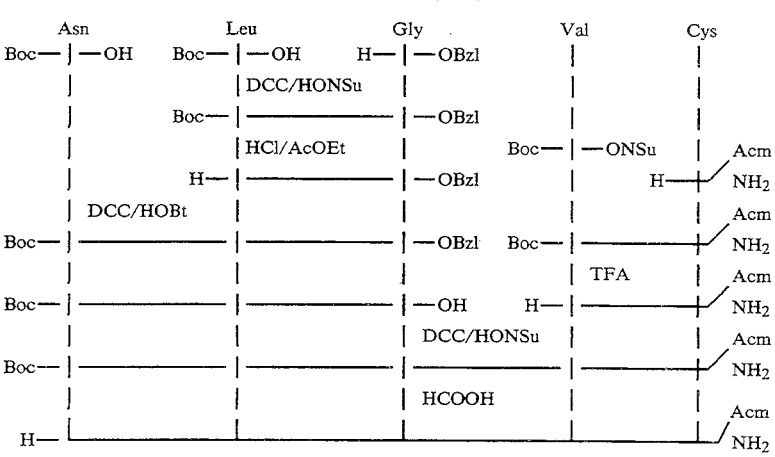

FIG. 2: Overall synthesis scheme

Boc-Val-Cys(Acm)-NH$_2$ 77.6 g (405 mmoles) Cys(Acm)NH$_2$ free base was dissolved in 1350 ml DMF and cooled to 4°–5° C. 85.0 g (270 mmoles) Boc-Val-ONSu was added and the reaction mixture stirred for one day at 4°–5° C. and for one day at room temperature. Filtration of the crude solution and preparative RP-HPLC chromatography analogous to the one described in example 1 gave fractions containing the pure product, which upon evaporation to dryness gives the product. Yield 66.4 g (63%).

TFA; Val-Cys(Acm)NH$_2$ 47.3 g (121.1 mmoles) Boc-Val-Cys(Acm)NH$_2$ was dissolved in 120 ml TFA. The product was precipitated after 15 minutes by addition of 450 ml diethylether under stirring. The stirring was kept for two hours to give a more homogeneous product. Filtration and drying under vacuum at 40° C. for one day gave the solid product. Yield 65.0 g (99%).

Boc-Leu-Gly-OBzl 102.2 g (442 mmoles) Boc-Leu-OH, 98.1 g (485 mmoles) Gly-OBzl.HCl and 55.9 g (478 mmoles) HONSu were dissolved in 760 ml dichloromethane added 54 ml N-methylmorpholine. Cooling to 4° C. and addition of a cold solution (4° C.) of 100.1 g (485 mmoles) DCC in 190 ml dichloromethane. The stirring was kept for one day at 4° C.

The crude solution was filtrated and the organic phase extracted one time with 500 ml 0.1M acetic acid and two times with 1000 ml of a saturated solution of sodium chloride. The organic phase was dried with MgSO$_4$ and the solvent evaporated under vacuum at 40° C. Yield 192.6 g crude product as an oil.

HCl,H-Leu-Gly-OBzl 192.6 g Boc-Leu-Gly-OBzl from above was dissolved slowly in 500 ml 3N HCl in ethylacetate under stirring. The reaction was finished after complete solution ($\approx 30$ minutes). The organic phase containing hydrochloric acid was evaporated to dryness under vacuum at 40° C. Further addition of 300 ml ethylacetate two times and evaporation to dryness gave the crude product as an oil. Yield 163.5 g.

Boc-Asn-Leu-Gly-OH 71.8 g (309 mmoles) Boc-Asn-OH, 163.5 g ($\approx 309$ mmoles) HCl,H-Leu-Gly-OBzl, 41.8 g HOBt (309 mmoles) and 34.0 ml (309 mmoles) NMM were dissolved in 250 ml DMF and the solution cooled to 2° C.

A cold solution (2° C.) of 63.8 g (309 mmoles) DCC in 80 ml DMF was added to the crude solution above. The combined solutions were slowly heated to room temperature and the stirring retained for one day.

The crude solution was filtrated to remove DCU and filled in a 1M sodium hydrogen carbonate solution under stirring, which gave precipitation of product and small amounts of HOBt.

Further washing two times of the crude product with 1.5 l of a 1M sodium hydrogen carbonate solution followed by filtration gave the purified product.

The crude Boc-Asn-Leu-Gly-OBzl was suspended in 2.0 l 50% ethanol. Addition of 10 g 10% Palladium on carbon and hydrogenation for one hour at 3 bar hydrogen pressure under stirring. The crude solution was filtrated and pH adjusted to 3.0 with a 1N sodium hydrochloric acid solution. Removal of ethanol under vacuum at 40° C. resulted in crystallisation of product. Filtration and drying under vacuum at 40° C. for 2 days gave the pure product. Yield 72.3 g (58%).

HAc,H-Asn-Leu-Gly-Val-Cys(Acm)-$NH_2$ 61.0 g (151.6 mmoles) Boc-Asn-Leu-Gly-OH and 19.2 g (165.3 mmoles) HONSu were dissolved in 500 ml DMF and the solution cooled to −10° C. A cold solution (−10° C.) of 34.12 g (165.3 mmoles) DCC in 170 ml DMF was added and the combined solutions stirred for one day at 4°–5° C.

Filtration of the crude solution to remove DCU and addition of a solution of 63.8 g (165.1 mmoles) TFA, H-Val-Cys(Acm)-$NH_2$ and 18.2 ml (165.1 mmoles) NMM in 200 ml DMF. The stirring was further continued for one hour at room temperature. Removal of solvent under vacuum at 40° C. gave the crude product Boc-Asn-Leu-Gly-Val-Cys(Acm)-$NH_2$. Yield 150.0 g.

The crude product was dissolved in 400 ml HCOOH and stirred for one day at room temperature. The solvent/reagent was removed under vacuum at 40° C. The residue was then dissolved in 3.0 l 50% ethanol (pH ≈3.0) and subjected to cation-exchange on a DOWEX AG 50×4 ($H^+$-form). Elution of the product with 1N $NH_4Ac$/50% EtOH gave fractions containing the product. Fractions containing product were concentrated to 400 ml and purified by RP-HPLC chromatography analogous to example 1. The pure product fractions were concentrated to 400 ml, sterile filtrated (0.22 μm filter) and freeze-dried for two days. Yield 27.0 g (33%).

| Analysis | |
|---|---|
| Water content by Karl Fisher titration: | 2.64 |
| Acetate content by GC: | 7.6% |
| Residual solvents: | DMF <0.05% |
| | Ethanol <0.1% |
| Amino acid analysis: | |
| Free amino acids: | <0.2% w/w |
| Asp: | 1.0 |
| Gly: | 1.0 |
| Val: | 1.0 |
| Cys: | identified |
| Leu: | 1.0 |
| Purity by HPLC (220 nm): | 98.9% |

EXAMPLE 5

Synthesis of HAc, H—Asn—Val—Cys(Acm)—$NH_2$

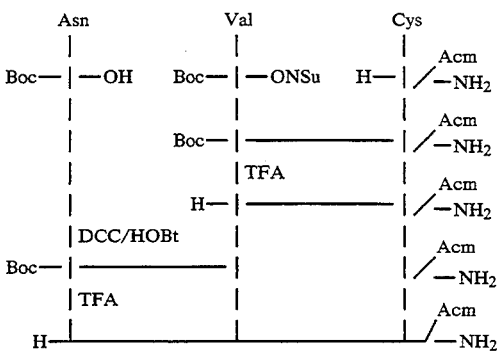

FIG. 3: Overall synthesis scheme

Boc-Asn-Val-Cys(Acm)-$NH_2$ 2.32 g (10 mmoles) Boc-Asn-OH, 4.45 g (11 mmoles) TFA,Val-Cys(Acm)-$NH_2$ prepared according to example 4 and 1.21 ml (11 mmoles NMM were dissolved in 20 ml DMF and cooled to 2° C.

An ice-cold solution of 2.17 g DCC in 5 ml DMF was added. The combined solutions were stirred for one day at 4°–5° C. Filtration and further dilution to 500 ml with 50% ethanol. Removal of HOBt by anion exchange on a DOWEX anion AG 1-X4 gel ($Ac^-$form).

Fractions containing product was evaporated to dryness and redissolved in 200 ml $H_2O$. The crude solution was purified by RP-HPLC chromatography analogous to example 1. The pure fractions containing product was evaporated to dryness under vacuum at 40° C. Yield 3.15 g (69%).

HAc,H-Asn-Val-Cys(Acm)-$NH_2$ 3.15 g (6.2 mmoles) Boc-Asn-Val-Cys(Acm)-$NH_2$ was dissolved in 15 ml TFA. The reaction was finished after complete solution (≈10 minutes). The product precipitated after addition of 350 ml diethylether. Filtration and drying under vacuum at 40° C. gave the product. Yield 2.2 g (76%).

The product was redissolved in 1000 ml 50% ethanol (pH≈5.0). Cation exchange on a DOWEX AG 50×4 ($H^+$-form). Elution of the product with 0.5N $NH_3$/50% ethanol. Fractions containing pure product was evaporated to dryness under vacuum at 40° C. Addition of 1 equivalent HOAc to the residual and freeze-drying for one day gave the pure product. Yield 2.2 g (76%).

Analysis

Purity by HPLC (220 nm):>95%

Pharmaceutical examples

The Therapeutic Activity: Regulation of the Intraocular Pressure in the Rabbit Eye Model The antiglaucoma pentapeptide lowers the experimentally increased intraocular pressure in the rabbit animal model, or it antagonizes, i.e. prevents the increase of pressure when it is applied simultaneously with the treatment which inflicts the increase of the pressure.

Adult rabbits of random breed and sex in groups of n=3–10 were employed. Weight 2,5–3,0 kg. The peptide was a freeze-dried powder, and was applied to the rabbit eye as a powder, or as drops, dissolved in 0.9% NaCl aqueous solution. Positive control was the commercial glaucoma drugs, either timololor pilocarpin, and negative control was 0.9% NaCl solution in water.

Stress induced Model Effects in Rabbits' Eyes

EXAMPLE 6

Effect of the antiglaucoma peptide

HAsnGlYGlyValCys(Acm)$NH_2$,HAc on stress induced ocular hypertensive rabbits. In total 60 mg peptide was applied as powder 4× daily over a period of four days, i.e. a total of 16 treatments. The amount of peptide per treatment was thus 3.75 mg which corresponds on a molar basis to the amount of Timolol used per treatment.

The local treatment was started on day 5 of glaucoma induction (i.e. afer 10 stress units), and the stress, that is the trauma, was continued during the treatment with the peptide.

The intraocular pressure is recorded in mm Hg

|  | Initial Pressure (Unstressed) | Pressure after 5 days of stress (Treatment starts) | Pressure after 10 days of stress (5 days of treatment) | Change in IOP | IOP lowering efficiency in relation to Timolol |
| --- | --- | --- | --- | --- | --- |
| 0.5% peptide | 19.0 | 32.0 | 16.5 | −15.5 | 150% |
| 0.25% Timolol | 19.0 | 30.0 | 19.5 | −10.5 | 100% |
| 0.9% saline | 18.0 | 29.0 | 32.0 | +14.0 |  |

EXAMPLE 7

Antagonizing effect of the antiglaucoma peptide on the stress induced intraocular pressure in the rabbit eye.

20 mg peptide was dissolved in 0.6 ml 0.9% NaCl aqueous solution and applied in aliquots of 60 μl four times daily over a period of 2.5 days.

The treatment was started at the beginning of the experiment simultaneously with stress units. Five stress units were applied at 12 hour intervals.

|  | Change in IOP (mm/Hg) After 2½ days | |
| --- | --- | --- |
|  | Absolute | Relative to Control |
| 0.9% Saline | +4.5 | — |
| Peptide | −4.7 | −9.2 |

No positive control with Timolol was included in this experiment.

EXAMPLE 8

Dose dependent effect of the antiglaucoma peptide on stress induced ocular hypertension in the rabbit eye.

A 1% and 0.1% solution of the peptide in 0.9% NaCl aqueous solution was applied four times (2 drops each time) for 5 days after an initial 5 day stress induction period. (Stress units at 12 hour intervals).

The intraocular pressure is recorded in mm Hg.

|  | Initial Pressure | Pressure after 5 days | Pressure after 10 days (5 days of treatment) |
| --- | --- | --- | --- |
| 0.9% saline | 18 | 29 | 32 |
| 1% peptide | 21 | 32 | 18 |
| 0.1% peptide | 18 | 28 | 15.5 |

EXAMPLE 9

Antagonizing effect of the antiglaucoma peptide and two analogues of it on the experimentally hypertensive rabbit eye.

Stress units were applied at 12 hour intervals over a period of 5½ days, i.e. 11 stress units. The peptides were applied 3× daily over this period as drops of a 0.5% solution in 0.9% NaCl in aqueous solutions.

The pressure is recorded as mm Hg.

|  | Initial Pressure | Pressure after 5 1/5 | Change in pressure |
| --- | --- | --- | --- |
| 0.9% Saline | 14 | 25 | +11 |
| Timolol | 15 | 16 | +1 |
| H—AsnGlyGlyValCys(Acm)NH₂ | 14 | 14 | 0 |
| H—AsnLeuGlyValCys(Acm)NH₂ | 15 | 16 | +1 |
| H—AsnAlaGlyValCys(Acm)NH₂ | 14 | 13 | −1 |

EXAMPLE 10

Antagonizing effect of one tetra- and two tripepride analogues of the anti-glaucoma peptide on the experimentally hypertensive rabbit eye.

Stress units were applied at 12 hour intervals over a period of 5½ days, i.e. 11 stress units. The peptides were applied 3× daily over this period as drops of a 1.0% solution in 0.9% NaCl in aqueous solution.

The ability of the tetra- and tripepride solutions to antagonize stress induced increase in intraocular pressure was then demonstrated by pressure measurements of this, showing a markedly lower pressure increase in all three treatments as compared to 0.9% saline.

Thus, all treatments with the three short analogues: AsnValCys(Acm)NH₂, AcGlyValCys(Acm)NH₂ and AsnLeuGlyCys(Acm)NH₂ showed a pressure increase smaller than 70% of that of negative saline controls.

Water Load Model Effects in Rabbits' Eyes

The studies utilized a "water load" animal model.

Thirty minutes before drug solution installation, rabbits were injected intraperitonally with 60 ml/kg of sterile distilled water for injection (30° C.) spiked with an antibiotic mixture (Sigma P9032).

At time zero, 50 μl of a drug solution was instilled to one eye and an equal volume of a saline solution was instilled to the other eye. The intraocular pressure in each eye was monitored at the time points indicated. The change in intraocular pressure (IOP) at each time point is computed by subtracting the IOP in the dosed eye from that in the undosed eye.

Plots of this data was made showing the IOP versus time including standard deviation for n=10. From these plots was assessed the maximal IOP effect, the time to reach this and the time for returning to a zero or insignificant level of intraocular pressure lowering effect. These figures may be taken as a measure of potency and duration of effect. As a measure of the full pharmaceutical effect at various dose levels was taken a sum figure of the area under the curves (AUC).

EXAMPLE 11

Effect of antiglaucoma pentapeptides on water load induced hypertension in the rabbit eye by single dose treatment.

A 0.5% solution of the peptides or 2.6% pilocarpine nitrate (positive control) in 0.9% NaCl aqueous solution was applied in one eye and 0.9% Nacl, also acting as negative control in the other eye, an IOP was measured in both eyes for 3 hours.

The intraocular pressure is recorded in mm Hg and the time in minutes:

| Treatment | Max. response Δ IOP | Time to max. response | Duration of effect |
| --- | --- | --- | --- |
| 0.9% | 0 | 0 | 0 |
| 2.6% pilocarpine nitrate | −5.0 | 30 | 120 |
| AsnGlyGlyVal-Cys(Acm)NH$_2$ | −5.0 | 30 | 120 |
| AsnLeuGlyVal-Cys(Acm)NH$_2$ | −5.5 | 30 | 120 |

EXAMPLE 12

Dose dependent effect of antiglaucoma pentapeptides on water load induced hypertension in the rabbit eye by single dose treatment.

A 0.25%, 0.5% of 1.0% solution of the peptides in 0.9% aqueous NaCl solution was applied in one eye and 0.9% NaCl to the other eye and IOP was measured in both eyes for 3 hours.

The intraocular pressure is recorded in mm Hg, the time in minutes and area under curve (AUC) in mm Hg×min.

| Peptide | Conc. | Max resp. Δ IOP | Time to max. resp. | Duration of effect | AUC |
| --- | --- | --- | --- | --- | --- |
| AsnGlyGlyVal-Cys(Acm)NH$_2$ | 0.25% | −2.0 | 30 | 80 | 160 |
| AsnGlyGlyVal-Cys(Acm)NH$_2$ | 0.5% | −5.0 | 30 | 120 | 360 |
| AsnGlyGlyVal-Cys(Acm)NH$_2$ | 1.0% | −4.0 | 30 | 120 | 410 |
| AsnLeuGlyVal-Cys(Acm)NH$_2$ | 0.25% | 0 | 0 | 0 | 0 |
| AsnLeuGlyVal-Cys(Acm)NH$_2$ | 0.5% | −5.5 | 30 | 120 | 400 |
| AsnLeuGlyVal-Cys(Acm)NH$_2$ | 1.0% | −5.0 | 30 | 120 | 550 |

3.0) and subjected to cation-exchange on a DOWEX AG 50×4 (H$^+$-form). Elution of the product with 1N NH$_4$Ac/50% EtOH gave fractions containing the product. Fractions containing product were concentrated to 400 ml and purified by RP-HPLC chromatography analogous to example 1. The pure product fractions were concentrated to 400 ml, sterile filtrated (0.22 μm filter) and freeze-dried for two days. Yield 27.0 g (33%).

| Analysis | |
| --- | --- |
| Water content by Karl Fisher titration: | 2.6% |
| Acetate content by GC: | 7.6% |
| Residual solvents: | DMF <0.55% |
|  | Ethanol <0.1% |
| Amino acid analysis: | |
| Free amino acids: | <0.2% w/w |
| Asp: | 1.0 |
| Gly: | 1.0 |
| Val: | 1.0 |
| Cys: | identified |
| Leu: | 1.0 |
| Purity by HPLC (220 nm): | 98.9% |

We claim:

1. A linear or cyclic peptide, or salt thereof, having an amino acid sequence selected from the group consisting of Asn-Gly-Gly-Val-Cys(Acm)NH$_2$, Asn-Leu-Gly-Val-Cys(Acm)NH$_2$, and Asn-Ala-Gly-Val-Cys-(Acm)NH$_2$.

2. A pharmaceutical composition of matter containing an effective amount of at least one peptide as in claim 1, in a pharmaceutically acceptable carrier, whereby intraocular pressure is lowered.

3. A method for treatment of glaucoma and intraocular hypertension, comprising administering to a mammal an effective amount of at least one peptide or pharmaceutically acceptable salt thereof according to claim 1.

* * * * *